US009540280B2

(12) United States Patent
Engqvist et al.

(10) Patent No.: US 9,540,280 B2
(45) Date of Patent: Jan. 10, 2017

(54) HYDRAULIC CEMENTS, METHODS AND PRODUCTS

(71) Applicant: OssDsign AB, Uppsala (SE)

(72) Inventors: Håkan Engqvist, Östhammar (SE); Jonas Åberg, Uppsala (SE)

(73) Assignee: OSSDSIGN AB, Uppsala (SE)

( * ) Notice: Subject to any disclaimer, the term of this patent is extended or adjusted under 35 U.S.C. 154(b) by 0 days.

(21) Appl. No.: 14/645,007

(22) Filed: Mar. 11, 2015

(65) Prior Publication Data
US 2015/0183687 A1 Jul. 2, 2015

Related U.S. Application Data

(63) Continuation of application No. 14/246,679, filed on Apr. 7, 2014, now Pat. No. 9,206,080, which is a continuation of application No. 13/128,034, filed as application No. PCT/IB2009/055042 on Nov. 12, 2009, now Pat. No. 8,709,149.

(60) Provisional application No. 61/113,840, filed on Nov. 12, 2008, provisional application No. 61/113,843, filed on Nov. 12, 2008, provisional application No. 61/113,852, filed on Nov. 12, 2008, provisional application No. 61/113,857, filed on Nov. 12, 2008, provisional application No. 61/184,413, filed on Jun. 5, 2009.

(51) Int. Cl.
C04B 12/02 (2006.01)
A61L 27/12 (2006.01)
C04B 28/02 (2006.01)
C04B 28/06 (2006.01)
C04B 28/14 (2006.01)
C04B 28/34 (2006.01)
A61K 6/06 (2006.01)
C04B 7/32 (2006.01)
C04B 111/00 (2006.01)

(52) U.S. Cl.
CPC ........... C04B 12/025 (2013.01); A61K 6/0631 (2013.01); A61K 6/0643 (2013.01); A61K 6/0675 (2013.01); A61L 27/12 (2013.01); C04B 7/32 (2013.01); C04B 28/02 (2013.01); C04B 28/06 (2013.01); C04B 28/145 (2013.01); C04B 28/344 (2013.01); C04B 2111/00137 (2013.01); C04B 2111/00836 (2013.01)

(58) Field of Classification Search
CPC ..... A61L 27/02; A61K 6/0643; A61K 6/0631; A61K 6/0675; C04B 7/32; C04B 12/025; C04B 14/06; C04B 14/306; C04B 29/008; C04B 22/124; C04B 24/383; C04B 28/02; C04B 28/06; C04B 28/145; C04B 28/344; C04B 40/065
See application file for complete search history.

(56) References Cited

U.S. PATENT DOCUMENTS

| | | |
|---|---|---|
| 5,152,836 A | 10/1992 | Hirano et al. |
| 5,338,356 A | 8/1994 | Hirano et al. |
| 5,605,713 A | 2/1997 | Boltong |
| 5,683,667 A | 11/1997 | Fulmer et al. |
| 5,782,971 A | 7/1998 | Constantz et al. |
| 5,783,217 A | 7/1998 | Lee et al. |
| 6,117,456 A | 9/2000 | Lee et al. |
| 6,206,957 B1 | 3/2001 | Wenz et al. |
| 6,338,810 B1 | 1/2002 | Carpena |
| 6,521,246 B2 | 2/2003 | Sapieszko et al. |
| 6,642,285 B1 | 11/2003 | Bohner et al. |
| 6,733,582 B1 | 5/2004 | Bohner et al. |
| 6,863,899 B2 | 3/2005 | Koblish et al. |
| 6,905,516 B1 | 6/2005 | Lemaitre et al. |
| 6,991,803 B2 | 1/2006 | Sapieszko et al. |
| 7,118,705 B2 | 10/2006 | Lin |
| 7,175,858 B2 | 2/2007 | Constantz et al. |
| 7,252,841 B2 | 8/2007 | Constantz et al. |
| 7,318,841 B2 | 1/2008 | Tofighi et al. |
| 7,351,280 B2 | 4/2008 | Khairoun et al. |
| 7,407,542 B2 | 8/2008 | Lemaitre et al. |
| 7,473,312 B2 | 1/2009 | Barralet et al. |
| 7,501,018 B2 | 3/2009 | Engqvist et al. |
| 7,754,246 B2 | 7/2010 | Mosley et al. |
| 8,591,645 B2 | 11/2013 | Engqvist et al. |
| 8,709,149 B2 | 4/2014 | Engqvist et al. |
| 2003/0082232 A1 | 5/2003 | Lee et al. |
| 2003/0199615 A1 | 10/2003 | Chaput et al. |
| 2006/0239884 A1 | 10/2006 | Chane-Ching et al. |

(Continued)

FOREIGN PATENT DOCUMENTS

| | | |
|---|---|---|
| CN | 1919357 A | 2/2007 |
| EP | 543765 A1 | 5/1993 |

(Continued)

OTHER PUBLICATIONS

Han et al, Acta Biomaterialia, 5:3165-3177 (2009).
Desai et al, Advances in Bioceramics and Biocomposites II, Ceramic Engineering and Science Proceedings, vol. 27, Issue 6, Wereszczak et al, Editor, Wiley, pp. 61-69 (Nov. 2006).
Hirayama et al, Journal of Research of the National Institute of Standards and Technology, 113(6):311-320 (2008).
Bohner et al, J. Biomaterials, 26(33):6423-6429 (Nov. 1, 2005).
Xu et al, Journal of Materials Science: Materials in Medicine, 18(7):1345-1353 (Feb. 3, 2007).
Barralet et al, J. Biomaterials, 25(11):2197-2203 (2004).

(Continued)

Primary Examiner — Anthony J Green
(74) Attorney, Agent, or Firm — Porter Wright Morris & Arthur LLP

(57) ABSTRACT

Non-aqueous hydraulic cement compositions comprise a non-aqueous mixture of (a) a non-hydrated powder composition comprising calcium silicate powder or calcium aluminate powder, and (b) non-aqueous water-miscible liquid. Hardened cements are formed from such hydraulic cement compositions, and methods of producing hardened cements, kits, and articles of manufacture employ such hydraulic cement compositions.

23 Claims, No Drawings

(56) References Cited

U.S. PATENT DOCUMENTS

| | | |
|---|---|---|
| 2006/0263443 A1 | 11/2006 | Chow et al. |
| 2007/0092856 A1 | 4/2007 | Chow et al. |
| 2007/0189951 A1 | 8/2007 | Constantz et al. |
| 2008/0027455 A1 | 1/2008 | Boudeville |
| 2008/0028992 A1 | 2/2008 | Lee et al. |
| 2008/0187571 A1 | 8/2008 | Clineff et al. |
| 2008/0206300 A1 | 8/2008 | Bohner et al. |
| 2009/0022771 A1 | 1/2009 | Lynn et al. |
| 2009/0220475 A1 | 9/2009 | Bohner et al. |
| 2010/0095870 A1 | 4/2010 | Insley et al. |
| 2010/0269736 A1 | 10/2010 | Chow et al. |
| 2010/0303888 A1 | 12/2010 | Barralet et al. |
| 2011/0014244 A1 | 1/2011 | Sapieszko et al. |
| 2011/0152195 A1 | 6/2011 | O'Mahony et al. |
| 2011/0158963 A1 | 6/2011 | Font Perez et al. |
| 2012/0058152 A1 | 3/2012 | Garcia de Castro Andrews et al. |
| 2013/0138114 A1 | 5/2013 | Lin et al. |

FOREIGN PATENT DOCUMENTS

| | | | |
|---|---|---|---|
| EP | 1023032 B1 | | 1/2002 |
| EP | 936929 B1 | | 6/2004 |
| EP | 1380313 B1 | | 5/2005 |
| EP | 1298103 B1 | | 5/2011 |
| JP | 1-100049 A | | 4/1989 |
| JP | 2003-12351 A | * | 1/2003 |
| WO | 00/07639 A1 | | 2/2000 |
| WO | 02/11781 A1 | | 2/2002 |
| WO | 03/024316 A2 | | 3/2003 |
| WO | 2004/093734 A2 | | 11/2004 |
| WO | 2005/074453 A2 | | 8/2005 |
| WO | 2005/077049 A2 | | 8/2005 |
| WO | 2007/047921 A2 | | 4/2007 |
| WO | WO 2008/008184 A2 | * | 1/2008 |
| WO | WO 2008/128347 A1 | * | 10/2008 |
| WO | 2009/077210 A1 | | 6/2009 |
| WO | 2010/092001 A1 | | 8/2010 |
| WO | 2011/009635 A1 | | 1/2011 |

OTHER PUBLICATIONS

Habraken et al, Advance Drug Delivery Reviews, 59(4-5):234-248 (Jun. 9, 2007).

Tamini et al, Acta Biomaterialia, 8(2):474-487 (Aug. 6, 2011).

Mirtchi et al, Biomaterials, 10(9):634-638 (1989).

Flautre et al, Journal of Biomedical Materials Research, 63(4):413-417 (2002).

Official Action dated Jan. 14, 2015 from corresponding EP 09 760 033.5.

* cited by examiner

HYDRAULIC CEMENTS, METHODS AND PRODUCTS

RELATED APPLICATIONS

The present application is a continuation application of U.S. application Ser. No. 14/246,679 filed Apr. 7, 2014, now U.S. Pat. No. 9,206,080 B2, which was a continuation application of U.S. application Ser. No. 13/128,034 filed Oct. 5, 2011, now U.S. Pat. No. 8,709,149 B2, which was a 371 of PCT/IB2009/055042 filed Nov. 12, 2009, which claimed priority under 35 U.S.C. 119 of U.S. Applications Nos. 61/113,840, 61/113,843, 61/113,852 and 61/113,857, all filed Nov. 12, 2008, and U.S. Application No. 61/184,413 filed Jun. 5, 2009, all of which applications and patents are incorporated herein by reference.

FIELD OF THE INVENTION

The present invention is directed to hydraulic cements, and, more particularly, to non-aqueous hydraulic cement compositions. The non-aqueous hydraulic cement compositions may be formed into hardened cements by contact with a hydration liquid or vapor. In a specific embodiment, the hydraulic cements are suitable for use as biomaterials for in vivo delivery, for example for bone and tooth restoration. The invention is also directed to hardened cements formed from such hydraulic cement compositions and to methods of producing hardened cements. The invention is further directed to kits and articles of manufacture including, inter alia, such hydraulic cement compositions.

BACKGROUND OF THE INVENTION

Self-hardening calcium phosphate cements (CPC) have been used for bone and tooth restoration and for local drug delivery applications. See, for example, Larsson et al, "Use of injectable calcium phosphate cement for fracture fixation: A review," *Clinical Orthopedics and Related Research*, 395: 23-32 (2002) and Oda et al, "Clinical use of a newly developed calcium phosphate cement (XSB-671D)," *Journal of Orthopedic Science*, 11(2): 167-174 (2006). The cements in powder form are typically mixed with an aqueous solution immediately before application. In the clinical situation, the ability of the surgeon to properly mix the cement powder and hydrating liquid and then place the cement paste in a defect within the prescribed time is a crucial factor in achieving optimum results. Specifically, the dry cement powder material needs to be mixed with an aqueous solution in the surgical setting, i.e., the operating room, transferred to an applicator, typically a syringe, and delivered to the desired location within the setting time. Conventional cements generally have a setting time of about 15-30 minutes. However, the methods used for mixing and transfer of cement for injection in the operating room are technically difficult and pose a risk for non-optimal material performance, e.g., early setting renders materials difficult to inject or causes phase separation, so called filter pressing. Further, for technical reasons and time constraints, the material is typically mixed with a hydrating liquid in bulk to form a paste and the paste is then transferred to smaller syringes for delivery. In practice, material is often wasted due to an early setting reaction, i.e., the hydrated material sets to a hardened cement prior to delivery to the desired location, or because too much material is being mixed. A solution to these problems that includes the possibility to deliver material in smaller quantities in a more controlled manner is thus desired.

There are two common setting chemistries for CPCs which result in two different end products after setting, hydroxyapatite (also referred to hydroxylapatite) and Brushite. The apatite product results from a neutral to alkaline reaction, whereas the Brushite product results from an acidic reaction. Apatite cements generally have longer resorption time than an acidic cement. See, for example, Constantz et al, "Histological, chemical, and crystallographic analysis of four calcium phosphate cements in different rabbit osseous sites," *Journal of Biomedical Materials Research*, 43(4): 451-461 (1998). However, the long resorption time for apatite cements can pose a problem in a clinical setting where the cement is used for bone restoration. That is, it is preferable to have a cement resorption rate similar to the formation rate of new bone so that the regeneration of the bone is not inhibited. This is not the case for many apatite cements. See, for example, Miyamoto et al, "Tissue response to fast-setting calcium phosphate cement in bone," *Journal of Biomedical Materials Research*, 37(4): 457-464 (1997). It has been shown that biphasic cements combining larger granules of, for example, β-tricalcium phosphate (β-TCP) in a matrix of brushite or apatite cement or alternative cements in combination with bioglass, result in better biological responses, i.e., faster bone in-growth, than cements without such additives. Another method to improve the biological response of cements, e.g., to provide faster bone in-growth, is via addition of silicon, strontium and/or fluoride to the cement composition. See, for example, Guo et al, "The influence of Sr doses on the in vitro biocompatibility and in vivo degradability of single-phase Sr-incorporated HAP cement," *Journal of Biomedical Materials Research Part A*, 86A(4): 947-958 (2008) and Camire et al, "Material characterization and in vivo behavior of silicon substituted alpha-tricalcium phosphate cement," *Journal of Biomedical Materials Research Part B-Applied Biomaterials*, 76B(2): 424-431 (2006). On the other hand, the acidic Brushite cements are difficult to use in a clinical setting due to their rapid setting reaction, involving the disadvantages discussed above.

Due to the fact that the cement precursor powders are anhydrous, it is difficult to handle powder with an average grain size below 1 micrometer. Such fine-grained materials have short shelf life and are also difficult to mix, especially in the operating room setting, due to very rapid setting times. The reactivity of the powders is related to the surface area, with a high surface area resulting in faster setting times and shorter shelf life. However, the strength of hardened cement materials obtained from fine-grained powders is higher than corresponding hardened cement materials formed from larger micrometer grain size materials, but the difficulties in handling and production discourage use of fine-grained powders.

In addition, injectable self-hardening biomaterials based on calcium silicates have been proposed for use in bone repair in orthopedics (see US 2006/0078590) and endodontics (see WO 94/24955). These self-hardening cements based on calcium silicates are similarly formed by mixing of powder and liquid to form a paste. However, the mixing procedure is often performed using a spatula or via a mechanical mixing system. Non-homogeneous mixing and the formation of air voids in the cement paste often result. Non-homogeneous mixed cement and/or air voids result in low mechanical strength and difficulties in delivering the cement through thin needles without obtaining phase separation between liquid and powder (the filter pressing effect). Moreover, these cements are fast setting and typically, in practice, the rheology of the cement can increase to such an extent that complete delivery by injection is impossible.

Self-hardening cements based on calcium aluminate cements have also been proposed to be used as biomaterial (see US 2008/0210125). The calcium aluminate cement materials have a beneficial mechanical strength profile compared to calcium phosphate cements, and in addition, the calcium aluminate materials are considered to be non-resorbable. However, due to the anhydrous nature of the calcium aluminate powders and their rapid hardening behavior, it is difficult to obtain a combined long shelf life and easy mixing to achieve optimal clinical results.

The problem of obtaining a proper mix of the powder material and hydrating liquid for optimum clinical results in apatite cements has been addressed in US 2006/0263443, US 2007/0092856, Carey et al, "Premixed rapid-setting calcium phosphate composites for bone repair," *Biomaterials,* 26(24): 5002-5014 (2005), Takagi et al, "Premixed calcium-phosphate cement pastes," *Journal of Biomedical Materials Research Part B-Applied Biomaterials,* 67B(2): 689-696 (2003), Xu et al, "Premixed macroporous calcium phosphate cement scaffold," *Journal of Materials Science-Materials in Medicine,* 18(7): 1345-1353 (2007), and Xu et al, "Premixed calcium phosphate cements: Synthesis, physical properties, and cell cytotoxicity," *Dental Materials,* 23(4): 433-441 (2007), wherein premixed pastes are described. In US 2006/0263443, for example, a powder composition for hydroxyapatite is premixed with an organic acid and glycerol to form a paste, which paste may subsequently be injected into a defect. The injected material hardens via the diffusion of body liquids into the biomaterial. The organic acid is added to increase resistance to washout and the end product after setting is apatite, which is known to have a long resorption time in vivo as described above. Also, compositions of β-tricalcium phosphate (β-TCP) and hydrated acid calcium phosphate in glycerin or polyethylene glycol have previously been described in CN 1919357. Han et al, "β-TCP/MCPM-based premixed calcium phosphate cements," *Acta Biomaterialia,* doi:10.1016/j.actbio.2009.04.024 (2009), also discloses premixed cements.

However, there is a continuing need to be able to efficiently prepare and safely deliver hydraulic cements, particularly for biomedical applications, i.e., hydraulic cements that overcome the above noted and/or other difficulties of conventional hydraulic cement materials, while optionally optimizing performance properties.

SUMMARY OF THE INVENTION

Accordingly, it is an object of the present invention to provide hydraulic cements, and hardened cements, methods, kits and articles of manufacture based on the hydraulic cements.

In one embodiment, the invention is directed to a non-aqueous, hydraulic cement composition which comprises a non-aqueous mixture of (a) a Brushite or Monetite-forming calcium phosphate powder composition, and (b) non-aqueous water-miscible liquid.

In another embodiment, the invention is directed to non-aqueous, hydraulic cement composition which comprises a non-aqueous mixture of (a) a non-hydrated powder composition comprising porous β-tricalcium phosphate (β-TCP) granules and at least one additional calcium phosphate powder, and (b) non-aqueous water-miscible liquid.

In another embodiment, the invention is directed to a non-aqueous, hydraulic cement composition which comprises a non-aqueous mixture of (a) a non-hydrated powder composition comprising calcium silicate powder, and (b) non-aqueous water-miscible liquid.

In a further embodiment, the invention is directed to a non-aqueous, hydraulic cement composition which comprises a non-aqueous mixture of (a) a non-hydrated powder composition comprising calcium aluminate powder, and (b) non-aqueous water-miscible liquid.

In another embodiment, the invention is directed to a non-aqueous, hydraulic cement composition which comprises a non-aqueous mixture of (a) a non-hydrated powder cement composition comprising nanopowders having a grain size of less than 1 micron, and (b) non-aqueous water-miscible liquid.

The invention is also directed to methods of producing a hardened cement with such compositions, hardened cements produced from such compositions, kits including such compositions, and articles of manufacture including such compositions.

The hydraulic cement compositions according to the invention are advantageous in that they avoid many of the point of use preparation difficulties of conventional hydraulic cement compositions, particularly when used as biomaterials, and may be easily and efficiently delivered to a desired location, without excessive material waste. Additionally, the hydraulic cement compositions according to the invention may be optimized for improved performance properties. These and additional objects and advantages of the present invention will be more fully appreciated in view of the following detailed description.

DETAILED DESCRIPTION

The non-aqueous, hydraulic cement compositions of the present invention are suitable for use in various applications. The present description refers to use of the compositions for in vivo applications, for example in bone and tooth repair. It will be appreciated that the present compositions are suitable for other in vivo applications as well as for non-biomaterial applications. The compositions of the invention contain non-hydrated powder and will hydrate upon contact with a hydrating liquid or vapor, typically water or an aqueous solution. The compositions may also comprise a small amount of partially hydrated powder, as will be discussed in further detail hereafter, provided that the partially hydrated powder does not change the essential nature of the powder composition, i.e., the powder composition does not set prematurely and is hydratable to form a set cohesive cement upon contact with a hydrating liquid or vapor.

In a first embodiment, the non-aqueous, hydraulic cement composition comprises a non-aqueous mixture of (a) a Brushite or Monetite-forming calcium phosphate powder composition, and (b) non-aqueous water-miscible liquid. In order to be Brushite-forming or Monetite-forming, the calcium phosphate powder composition is acidic, i.e., the pH of the hydraulic cement composition during setting is less than about 6.0. Thus, in a broad embodiment, the calcium phosphate powder is acidic and an acidic cement is formed. In a specific embodiment, the Brushite or Monetite-forming calcium phosphate powder composition comprises an acidic phosphate, for example, monocalcium phosphate monohydrate (MCPM), anhydrous monocalcium phosphate, phosphoric acid, pyrophosphoric acid, or a mixture thereof. In a more specific embodiment, the Brushite or Monetite-forming powder composition comprises monocalcium phosphate monohydrate (MCPM), anhydrous monocalcium phosphate, or a mixture thereof. The Brushite or Monetite-forming powder composition may further comprise one or more basic calcium phosphates, as long as the pH of the hydraulic cement composition during setting is less than about 6.0 to result in the Brushite or Monetite cement. Thus, the Brushite or Monetite-forming calcium phosphate powder composition may further comprise one or more calcium phosphates selected from the group consisting of anhydrous dicalcium phosphate, dicalcium phosphate dihydrate, octacalcium phosphate, α-tricalcium phosphate, β-tricalcium phosphate, amorphous calcium phosphate, calcium-deficient hydroxyapatite, non-stoichiometric hydroxyapatite, and tetracalcium phosphate.

In additional embodiments, the Brushite or Monetite-forming powder composition may include additional powder components and/or other additives as desired. Exemplary powder additives include, but are not limited to, $Na_2HPO_4$, calcium sulphate, calcium carbonate, calcium oxide (CaO), calcium hydroxide ($Ca(OH)_2$), magnesium-containing powder, silica powder, a fluoride compound, a strontium compound, or the like. In one specific embodiment, the Brushite or Monetite-forming calcium phosphate powder composition comprises up to 15 weight % of the powder composition of a magnesium source, i.e., a magnesium-containing powder or compound, which may be added to stabilize an end-product of the setting reaction between the components. The solubility of the magnesium source is preferably less than 100 g/L. In another specific embodiment, the Brushite or Monetite-forming calcium phosphate powder composition comprises up to 20 weight % of the powder composition of silica, which may be added to optimize the biological response and/or to increase the mechanical strength of the hardened material. Non-limiting examples include microcrystalline silica with a grain size of below 50 nm and calcium silicate, for example, $CaOSiO_2$, $(CaO)_3SiO_2$, and/or $(CaO)_2SiO_2$, and bioglass, a non-limiting example of which includes a composition of 45.0 wt % $SiO_2$, 24.5 wt % CaO 24.5 wt % $Na_2O$ and 6.0 wt % $P_2O_5$, and other similar formulations as described by Flautre et al, "Bone colonization of beta-TCP granules incorporated in brushite cements," *Journal of Biomedical Materials Research*, 63(4): 413-417 (2002). In one embodiment, the silica has a grain size of not greater than 300 micrometers.

In another specific embodiment, the Brushite or Monetite-forming powder composition comprises up to 10 weight % of the powder composition of fluoride or strontium or combinations thereof. In a specific embodiment, the powder composition comprises NaF, which may be added to optimize the biological response to the hardened material. In another specific embodiment, the Brushite or Monetite-forming calcium phosphate powder composition comprises up to 40 weight % of the powder composition of calcium carbonate. Calcium carbonate may be added to control the resorption time of the hardened material. The calcium carbonate can be, for example, calcite, vaterite, aragonite or amorphous calcium carbonate, or combinations thereof.

In a second embodiment, the non-aqueous, hydraulic cement composition comprises a non-aqueous mixture of (a) a non-hydrated powder composition comprising porous β-tricalcium phosphate (β-TCP) granules and at least one additional calcium phosphate powder, and (b) non-aqueous water-miscible liquid. The porous β-TCP granules modify the resorbtion rate and bone remodelling of the hardened cement which is formed upon hydration and setting. The granules generally comprise agglomerated powders and the porosity of the granules comprises pores formed between individual powder grains in the agglomerates. In a specific embodiment, the granule size is from about 10 to about 3000 micrometers. In a further embodiment, the granule size is from about 10 to about 1000 micrometers and may be selected to optimize mechanical and/or biological properties of the resulting hardened cement. In a specific embodiment, the granule porosity is at most 80 vol % and the pore size is at most 200 micrometers.

In a specific embodiment, the weight ratio of porous β-TCP granules to additional calcium phosphate powder in the non-hydrated powder composition is in a range about 1:3 to about 3:1, or, more specifically, in a range of about 2:1 to about 1:2. The additional calcium phosphate powder may comprise an acidic powder, a basic powder, or a mixture thereof. In one embodiment, the additional calcium phosphate powder comprises one or more of monocalcium phosphate monohydrate (MCPM), monocalcium phosphate anhydrous (MCPA), dicalcium phosphate anhydrous (DCPA), dicalcium phosphate dihydrate (DCPD), octacalcium phosphate (OCP), α-tricalcium phosphate (α-TCP), amorphous calcium phosphate, calcium-deficient hydroxyapatite (HA), non-stoichiometric HA, ion-substituted HA, and tetracalcium phosphate (TTCP). In a more specific embodiment, the additional calcium phosphate powder comprises an acidic powder and, more specifically, monocalcium phosphate monohydrate (MCPM), anhydrous monocalcium phosphate, or a mixture thereof. In yet a further embodiment, the additional calcium phosphate powder comprises an acidic powder, for example, monocalcium phosphate monohydrate (MCPM), anhydrous monocalcium phosphate, or a mixture thereof, and a basic powder, for example, tetracalcium phosphate, octacalcium phosphate (OCP), α-tricalcium phosphate (α-TCP), amorphous calcium phosphate, calcium-deficient HA, non-stoichiometric HA, ion-substituted HA, tetracalcium phosphate (TTCP) or combinations thereof. In a specific embodiment, the basic powder comprises at least 30 wt. % of the powder composition. The components of the precursor powder compositions are chosen in such an amount that either (i) the pH of the cement paste during setting is lower than 6, or (ii) the pH of the cement paste during setting is above 6, or (iii) a combination of (i) and (ii) with an first initial pH below 6 followed by a pH above 6 during the setting reaction, or (iv) a first neutral pH followed by a pH below 6 during the setting reaction. Depending on the pH of the powder composition during setting of the cement material, the end-product may comprise amourphous calcium phosphate hydrate, hydroxyapatite, ion-substituted hydroxyapatite, dicalcium phosphate dihydrate (brushite) or $Ca(HPO_4)$ (monetite), or combinations thereof.

According to one specific embodiment, the precursor powder composition is acidic and comprises (a) a basic calcium phosphate component comprising the porous β-TCP granules and optionally tetra calcium phosphate (TTCP) and/or amorphous calcium phosphate, and (b) an acidic phosphate, non-limiting examples of which include monocalcium phosphate monohydrate (MCPM), anhydrous monocalcium phosphate, phosphoric acid, pyrophosphoric acid or combinations thereof. The weight ratio between components (a) and (b) may be in the range of about 3:1 to about 1:3. The components of the powder composition are chosen such that (i) the pH of the cement paste during setting is lower than 6.0; and (ii) the end-product of the setting reaction comprises dicalcium phosphate dihydrate (brushite) or $Ca(HPO_4)$ (monetite) or a combination thereof.

In an alternate embodiment, the precursor powder composition is basic (apatitic) and comprises (a) a basic calcium phosphate component comprising the porous β-TCP granules and optionally tetra calcium phosphate (TTCP) and/or amorphous calcium phosphate, and (b) an acidic phosphate, non-limiting examples of which include monocalcium phosphate monohydrate (MCPM), anhydrous monocalcium phosphate, phosphoric acid, pyrophosphoric acid or combinations thereof. The components of the apatitic precursor powder compositions are chosen such that (i) the pH of the cement paste during setting is higher then 6; and (ii) the end-product of the setting reaction comprises amorphous calcium phosphate hydrate, hydroxyapatite, ion-substituted hydroxyapatite, or combinations thereof.

The calcium phosphate powder composition may include additional powder components and/or other additives as desired. Exemplary powder additives include, but are not limited to, $Na_2HPO_4$, calcium sulphate, calcium carbonate, calcium oxide (CaO), calcium hydroxide ($Ca(OH)_2$), magnesium-containing powder, silica powder, a fluoride compound, a strontium compound, or the like. In one specific embodiment, the calcium phosphate powder composition comprises up to 15 weight % of the powder composition of a magnesium source, i.e., a magnesium-containing powder or compound, which may be added to stabilize an end-product of the setting reaction between the components. The solubility of the magnesium source is preferably less than 100 g/L. In another specific embodiment, the calcium phosphate powder composition comprises up to 20 weight % of the powder composition of silica, which may be added to optimize the biological response and/or to increase the mechanical strength of the hardened material. Non-limiting examples include microcrystalline silica with a grain size of below 50 nm and calcium silicate, for example, $CaOSiO_2$, $(CaO)_3SiO_2$, and/or $(CaO)_2SiO_2$, and bioglass, a non-limiting example of which includes a composition of 45.0 wt % $SiO_2$, 24.5 wt % CaO 24.5 wt % $Na_2O$ and 6.0 wt % $P_2O_5$, and other similar formulations as described by Flautre et al, "Bone colonization of beta-TCP granules incorporated in brushite cements," *Journal of Biomedical Materials Research*, 63(4): 413-417 (2002). In one embodiment, the silica has a grain size of not greater than 300 micrometers.

In another specific embodiment, the calcium phosphate powder composition comprises up to 10 weight % of the powder composition of fluoride or strontium or combinations thereof. In a specific embodiment, the powder composition comprises NaF, which may be added to optimize the biological response to the hardened material. In another specific embodiment, the calcium phosphate powder composition comprises up to 40 weight % of the powder composition of calcium carbonate. Calcium carbonate may be added to control the resorption time of the hardened material. The calcium carbonate can be, for example, calcite, vaterite, aragonite or amorphous calcium carbonate, or combinations thereof.

In a third embodiment of the invention, the non-aqueous, hydraulic cement composition comprises a non-aqueous mixture of (a) a non-hydrated powder composition comprising calcium silicate powder, and (b) non-aqueous water-miscible liquid. When hydrated, the composition forms a calcium silicate hydrate. In a specific embodiment, the powder composition comprises 20-100 weight % calcium silicate, for example, $CaOSiO_2$, $(CaO)_3SiO_2$, and/or $(CaO)_2SiO_2$. In one embodiment, to optimize a clinically acceptable setting time, the composition includes $(CaO)_3SiO_2$ or $(CaO)_2SiO_2$ or combinations thereof, or, more specifically, $(CaO)_3SiO_2$. It is often difficult to obtain a 100% pure phase composition and therefore trace amounts of all calcium silicate phases may be present in the composition.

In one embodiment, the powder composition may optionally comprise, in addition to the calcium silicate, one or more components selected from the group consisting of calcium phosphates, calcium sulfates, and magnesium-containing powder. In a more specific embodiment, the powder composition comprises at least about 50 weight % calcium silicate and from about 5 to about 50 weight %, more specifically from about 5 to about 30 weight %, of a calcium phosphate powder. In a further embodiment, the calcium phosphate powder forms an acidic calcium phosphate cement and may be employed to increase the resorption rate and/or decrease the setting time, and comprises a mixture of a basic calcium phosphate and an acidic calcium phosphate. In a more specific embodiment, the calcium phosphate powder which forms an acidic calcium phosphate cement may comprise a mixture of (i) β-tricalcium phosphate (β-TCP), and (ii) monocalcium phosphate monohydrate and/or anhydrous monocalcium phosphate. Alternatively, the calcium phosphate powder forms a basic calcium phosphate cement and may be employed to decrease the setting time. The calcium phosphate powder which forms a basic calcium phosphate cement may comprise one or more calcium phosphates selected from the group consisting of anhydrous monocalcium phosphate, anhydrous dicalcium phosphate, dicalcium phosphate dihydrate, octacalcium phosphate, α-tricalcium phosphate, β-tricalcium phosphate, amorphous calcium phosphate, calcium-deficient hydroxyapatite, non-stoichiometric hydroxyapatite, and tetracalcium phosphate.

In another specific embodiment, the powder composition may optionally comprise, in addition to the calcium silicate, from about 5 to about 60 weight %, more specifically from about 5 to about 50 weight %, and even more specifically from about 5 to about 30 weight %, of calcium sulfate powder to increase the resorption rate and/or decrease the setting time. The calcium sulfate powder may be of the dihydrate, hemihydrate (alfa or beta or combinations thereof), and/or anhydrate structures. In one embodiment, calcium sulfate of the alpha-hemihydrate structure is preferred owing to its higher strength and lower rapid setting time.

In yet another specific embodiment, the powder composition may optionally comprise, in addition to the calcium silicate, from about 0.1 to about 15 weight % of a magnesium source, i.e., a magnesium-containing powder or compound, which may be added to stabilize an end-product of the setting reaction between the components. The solubility of the magnesium source is preferably less than 100 g/L. In further embodiments, the powder composition may comprise a pH regulating agent, for example in an amount of from about 0.1 to about 15 weight %, and/or a hardening accelerator, for example, calcium chloride, in an amount of from about 0.01 to about 10 weight %, more specifically in an amount of from about 1 to about 7 weight %.

In a fourth embodiment, the invention is directed to a non-aqueous, hydraulic cement composition comprising a non-aqueous mixture of (a) a non-hydrated powder composition comprising calcium aluminate powder, and (b) non-aqueous water-miscible liquid. The calcium aluminate powder comprises one or more powders selected from the group consisting of $(CaO)_3Al_2O_3$, $(CaO)_{12}(Al_2O_3)_7$, $(CaO)Al_2O_3$, $CaO(Al_2O_3)_2$, and $CaO(Al_2O_3)_6$. In a specific embodiment, wherein the setting time may be optimized, the calcium aluminate powder comprises one or more powders selected from the group consisting of $(CaO)_3Al_2O_3$, $(CaO)_{12}(Al_2O_3)_7$, and $(CaO)Al_2O_3$. In a more specific embodiment, the calcium aluminate powder comprises $(CaO)_{12}(Al_2O_3)_7$ and/ or $(CaO)Al_2O_3$ and in a more specific embodiment, the calcium aluminate powder comprises $(CaO)Al_2O_3$. In one embodiment, the calcium aluminate is amorphous, more specifically amorphous $(CaO)_{12}(Al_2O_3)_7$. Upon hydration, a hardened cement comprising calcium aluminate hydrate is formed.

In a specific embodiment, the powder composition comprises at least about 10 weight %, or from about 10 to about 100 weight %, of calcium aluminate powder. In a more specific embodiment, the powder composition comprises at least about 50 weight percent of the calcium aluminate powder to provide high strength. In a further embodiment, the powder composition comprises from about 3 to about 60 weight %, specifically from about 3 to about 50 weight %, more specifically from about 10 to about 30 weight %, of an agent operable to increase radio-opacity of the composition. Examples of such agents include, but are not limited to, zirconium dioxide, barium sulfate, iodine and strontium compounds and combinations thereof. The increased radio-opacity provided by such an agent is important to increase safety during injection (high visibility compared to bone tissue) and follow up when set in vivo. The powder composition may also optionally include microcrystalline silica which may be added to control expansion properties of the material. In one embodiment, the powder composition comprises from about 0.1 to about 15 weight %, more specifically from about 0.1 to about 5 weight %, of microcrystalline silica.

In an additional embodiment, the powder compositions comprising calcium aluminate may include one or accelerating additives to reduce the setting time required to form hardened cement. An exemplary, non-limiting accelerating additive is lithium chloride. In one embodiment, the accelerating additive, including lithium chloride or the like, is employed in an amount of from about 0.01 to about 3 weight % of the powder composition, or more specifically from about 0.01 to about 0.5 weight %.

In any of the first, second, third and fourth embodiments of the invention discussed above, the use of fine-grained powder materials is suitable. The grain size of the cement components according to the present invention is preferably below about 300 micrometers, more preferably below about 50 micrometers and most preferably below about 20 micrometers. A smaller grain size is normally preferred since it gives a faster setting reaction and a more homogenous and strong cement. The grain size corresponds to the d99 grain size wherein d99 represents the volume diameter 99% and means that 99% of the particles are below the given size, measured using conventional techniques such as laser diffraction. In a further embodiment, a portion or all of the powders may comprise nano-sized materials. Nano-sized materials generally have a more homogenous microstructure, which leads to better mechanical properties. While use of nano-sized fine-grained cement powders in conventional cements decreases setting times to levels that are not favorable in a clinical setting, this disadvantage is avoided when using the present invention materials. That is, it is still possible to use fine-grained materials while obtaining favorable setting times.

Thus, in a fifth embodiment, the invention is directed to a non-aqueous, hydraulic cement composition, comprising a non-aqueous mixture of (a) a non-hydrated powder cement composition comprising nanopowders having a grain size of less than 1 micron, more specifically less than about 500 nm, even more specifically less than about 300 nm, and (b) non-aqueous water-miscible liquid. In a specific embodiment, the powder composition comprises nanopowders having a grain size of less than about 100 nm. The powder composition may comprise any of the powder compositions discussed above with respect to the first, second, third and fourth embodiments, or may comprise another non-hydrated powder cement composition suitable for forming a hardened cement upon hydration.

In one embodiment, the powder composition comprises one or more calcium phosphate nanopowders selected from the group consisting of anhydrous monocalcium phosphate, anhydrous dicalcium phosphate, dicalcium phosphate dihydrate, octacalcium phosphate, α-tricalcium phosphate, β-tricalcium phosphate, amorphous calcium phosphate, calcium-deficient hydroxyapatite, non-stoichiometric hydroxyapatite, and tetracalcium phosphate (TTCP). In a specific embodiment, the powder composition comprises an acidic calcium phosphate cement comprising from about 30 to about 70 weight % of basic calcium phosphate powder and from about 30 to about 70 weight % acidic calcium phosphate powder, and at least a portion of the calcium phosphate powders are nanopowders, and wherein the composition exhibits a pH less than about 6.0 upon hydration and is operable to form Brushite or Monetite upon hydration. In a more specific embodiment, the basic calcium phosphate powder comprises α-tricalcium phosphate, β-tricalcium phosphate, or amorphous calcium phosphate, and the acidic calcium phosphate powder comprises monocalcium phosphate monohydrate, anhydrous monocalcium phosphate, or a mixture thereof. In yet a more specific embodiment, the acidic cement powder composition further comprises from about 0.1 to about 15 weight % of a source of magnesium, i.e, magnesium-containing powder, having a solubility of less than 100 g/L.

In another embodiment, the powder composition comprises nanopowders of calcium silicate, for example, one or more of $(CaO)_3SiO_2$, $(CaO)_2SiO_2$, and $(CaO)SiO_2$. In a specific embodiment, the powder composition comprises nanopowders of one or more of $(CaO)_3SiO_2$ and $(CaO)_2SiO_2$, and in a more specific embodiment, the powder composition comprises nanopowders of $(CaO)_3SiO_2$. In another embodiment, the powder composition comprises calcium silicate and silica nanopowders.

The first, second, third, fourth and fifth embodiments of the invention as described above employ powder compositions having non-hydrated powders therein. As a result, upon hydration, i.e., contact with a hydrating liquid or vapor, a hardened cement will be formed. In a specific embodiment, a portion of the powder compositions may employ a partially hydrated powder, for example a powder that has partially reacted with water. In a more specific embodiment, the powder composition may comprise less than about 20 weight percent, more specifically less than about 10 weight percent, more specifically less than about 5 weight percent, of partially hydrated powders. In more specific embodiments, the powder composition may comprise less than about 4 weight percent, more specifically less than about 2 weight percent, more specifically less than about 1 weight percent, of partially hydrated powders. In a further embodiment, a prehydrated powder may be added, for example to accelerate the setting reaction.

In the first, second, third, fourth and fifth embodiments of the invention as described above, any suitable, non-aqueous water-miscible liquid may be employed. Exemplary liquids include, but are not limited to, glycerol, propylene glycol, poly(propylene glycol), poly(ethylene glycol) and combinations thereof, and related liquid compounds and derivatives, i.e., substances derived from non-aqueous water miscible substances, substitutes, i.e., substances where part of the chemical structure has been substituted with another chemical structure, and the like. Certain alcohols may also be suitable as mixing liquid. In a specific embodiment, the liquid is glycerol.

The powder to non-aqueous water-miscible liquid weight to volume ratio (P/L) may suitably be in a range of from about 0.5 to about 10, more specifically from about 1 to about 7, and more specifically from about 2.5 to about 7, or from about 2.5 to about 5, for better handling and mechanical strength. These ratios are suitable even if two or more liquids are used in combination.

The hydraulic cement compositions of the invention may also include agents that facilitate a fast diffusion of water formed in situ into the paste which is formed by the powder composition and the non-aqueous liquid. In one embodiment, the agent comprises a surfactant, more specifically a non-ionic surfactant, an example of which includes, but is not limited to, a polysorbate. The amount of surfactant may from about 0.01 to about 5 weight % of the powder composition, or, more specifically, from about 0.1 to about 1 weight %.

The hydraulic cement compositions of the invention may also include one or more porogens to provide a macroporous cement product. A macroporous cement product facilitates fast resorbtion and tissue in-growth. The porogen may include sugars and other fast-resorbing agents. The amount of porogen may suitably be from about 5 to about 30 weight % of the powder composition.

The hydraulic cement compositions of the invention may also include one or more non-toxic gelling agents to enhance cohesiveness and washout resistance of the compositions upon delivery. Exemplary gelling agents include, but are not limited to, chitosan, collagen, gum, gelatin, alginate, cellulose, polyacrylic acid (PAA), polymethacrylic acid (PMA), neutral polyacrylic and/or polymethacrylic acid (e.g. Na-PAA, Na-PMA acid), hydroxypropylmethyl cellulose (HPMC), hydroxymethyl cellulose (HMC), and carboxymethyl cellulose (CMC), and combinations thereof. The amount of gelling agent represents suitably from about 0.1 to about 7 weight % of the powder composition, more specifically from about 0.1 to about 2 weight %.

According to another embodiment, the hydraulic cement compositions of the invention may also include one or more active pharmaceutical ingredients (API). Exemplary APIs include, but are not limited to, one or more agents selected from the group consisting of an anti-cancer agent, an antibacterial agent, for example, Gentamicin or Tobramicin, an analgesic agent, a bisphosphonate, a bone growth promoter, for example a bone morphogenetic protein (such as BMP 2 or BMP 7), and an anti-inflammatory agent. The API may comprise from about 0.01 to about 20 weight % of the hydraulic cement composition. The addition of API to the hydraulic cement compositions provides a product exhibiting a local slow release of the drug to the implantation site.

Optionally, the hydraulic cement compositions of the invention may also include one or more agents for increasing radio-opacity of the compositions. Non-limiting examples include iodine, strontium compounds (e.g., Sr-carbonate), barium compounds (e.g., Ba-sulphate and Ba-carbonate), bismuth compounds and zirconium dioxide. When used, such agents are suitably present in amounts of from about 5 to about 40 weight %, more specifically from about 15 to about 30 weight % of the hydraulic cement compositions. The radio-opacity is advantageous to provide increased visibility (high contrast compared to bone tissue) of the material during injection and when implanted. In a specific embodiment, the grain size of the radio opacity additives is normally below 100 micrometer.

Optionally, the hydraulic cement compositions of the invention may also include fibers to reinforce the cement. Non-limiting examples include fibers comprising polypropylene, nylon, aramid, carbon, E-glass, polyglactin, or polyamide. When used, such fibers are suitably present in amounts of from about 1 to about 30 volume %, more specifically from about 2 to about 15 volume %, of the hydraulic cement compositions. Fiber reinforcement will increase the strength of the cement, especially the flexural strength.

The hydraulic cement compositions are formed into hardened cement materials by contact with a hydrating liquid or vapor. In a specific embodiment, a hydrating liquid is employed. The hydration liquid may be any polar liquid, such as water and other polar protic solvents (e.g. alcohol). The hydrating liquid is suitably water or an aqueous solution. The hydration liquid can optionally have a pH within the range of 1-9. The hydraulic cement compositions in the form of a premixed paste may be delivered, for example to an implant site when used as a biomaterial, using a syringe or spatula. The hydraulic cement compositions may be shaped in vivo, and subsequently be hydrated or be allowed to hydrate in vivo. Optionally, a water-containing liquid can be added to the premixed paste before delivery, for example, before injection. This may be achieved by use, for example, of a double-barrel syringe with the described premixed paste in one and the hydrating liquid, i.e., water or a water-containing liquid, in the other. The two may then be mixed using a mixing tip during injection.

The hydraulic cement compositions in the form of a premixed paste can also be packaged in a vacuum package to reduce the amount of air voids in the paste and thus increase the final strength of the hardened material. Air voids reduce the strength of the set material and reduction of air voids is therefore important. The hydraulic cement compositions may be conveniently mixed and packaged under vacuum conditions. Preferably the hydraulic cement compositions are vacuum-mixed (e.g. in a Ross Vacuum Mixer Homogenizer).

In another embodiment of the invention, the hydraulic cement compositions may be provided as a component of a kit, for example in combination with a separately contained quantity of hydrating liquid. In a specific embodiment, the kit comprises several prefilled syringes of the same or of various sizes. One non-limiting example is a kit with several 2 ml prefilled syringes. Another non-limiting example is a kit with several 1 ml prefilled syringes. Thus, another embodiment of the invention comprises an article of manufacture comprising a hydraulic cement composition in a dispensing container, more specifically a syringe.

The described hydraulic cement compositions are suitably employed as injectable in situ-setting biomaterials. The compositions can be used as any implant, more specifically as a bone implant, more specifically as dental or orthopedic implant. In a specific embodiment, the hydraulic cement compositions are suitable used as material in cranio maxillofacial defects (CMF), bone void filler, trauma, spinal, endodontic, intervertebral disc replacement and percutaneous vertebroplasty (vertebral compression fracture) applications.

Various embodiments of the invention are illustrated in the following Examples.

Example 1

This example demonstrates a hydraulic cement composition according to the invention. Specifically, a premixed cement powder composition comprising monocalcium phosphate monohydrate ($Ca(H_2PO_4)_2$—$H_2O$) (Sigma) and β-tricalcium phosphate (β-TCP, $β$-$Ca_3(PO_4)_2$) (Fluka), having a particle size <100 μm, is prepared. A molar ratio of 1:1 for β-TCP and MCPM is used. Two additives are used, namely a surfactant, polysorbate 20 (PS), and a gelling agent, hydroxypropyl methylcellulose (HPMC). β-TCP and MCPM are first mixed, then the HPMC is added. The polysorbate is first mixed with glycerol separately and then added to the powder, in amounts according to Table 1. The powder/liquid ratio (P/L) is varied between 3.5 and 4.75 g/ml. The mixture is stirred for 5 minutes thoroughly so that a homogenous cement paste is obtained, which is injected into a cylindrical rubber mould, open at both ends. The mould is immersed in 40 ml phosphate buffered saline solution (PBS, pH 7.4) at 37° C. and kept in a sealed beaker. After 24 hours, the samples are removed from the mould. For comparison, the described powder composition is mixed directly with water.

Compressive Strength (CS):

For the CS measurement, samples which are 6 mm in diameter and 12 mm in height are used. CS is measured after 24 h of storage in PBS solution.

Setting Time (ST):

The ST is measured using the Gillmore needle method. For the ST measurements, a cylindrical teflon mould is used, 6 mm in diameter and 3 mm in height. The measurements are started when the mould is immersed in 40 ml of PBS at 37° C. The bottom and the top of the mould are covered with a polycarbonate filter pore size 5 μm (Millipore).

In Vitro Study:

Both set premixed cement and the premixed paste are evaluated in vitro using mesenchymal stem cells. The set cement has a P/L of 4.75 and the paste has a P/L 4.3.

In Vivo Study:

Premixed cement is injected subcutaneously in rats after which the systemic immunologic response is evaluated. A P/L of 4 is used.

Results:

The amounts of additives, the setting times, and the compressive strengths after 24 hours in PBS at 37° C. are set forth in Table 1:

TABLE 1

| P/L, g/ml | B-TCP/ MCPM, % | PS, %* | HPMC, % | ST, min | CS, MPa |
|---|---|---|---|---|---|
| 3.5 | 97 | 0.5 | 3 | 42 | 6 |
| 4.75 | 100 | — | — | 29 | 10 |
| 4.75 | 97 | — | 3 | 29 | 9 |
| 4.75 | 97 | 1 | 3 | 29 | 9 |
| 4.75 | 100 | 1 | — | 29 | 10 |

*Liquid percent

The results show that an acidic premixed material system with clinically acceptable setting time could be achieved, combined with a strength development. The in vitro study showed that the mesenchymal stem cells could migrate to and differentiate on both set premixed cement and unreacted premixed paste. In vivo studies showed no systemic immunologic response. The same precursor cement material mixed directly with water had too short of a setting time to mould a sample that could be strength-tested, and no data could thus be obtained.

Example 2

This example demonstrates a hydraulic cement composition according to the invention. Specifically, a premixed cement comprising monocalcium phosphate monohydrate ($Ca(H_2PO_4)_2$—$H_2O$) (Scharlau) and β-tricalcium phosphate (β-TCP, $β$-$Ca_3(PO_4)_2$) (Fluka), having a particle size <100 μm, is prepared. A molar ratio of 1:1 for β-TCP and MCPM is used. Two additives are used, namely Zirconia ($ZrO_2$, Sigma), particle size 5 μm, and β-TCP granules, size 50-150 μm (Cerasorb), in amounts according to Table 2. The powders are first mixed, then glycerol is added. The powder/liquid ratio (P/L) is varied between 4 and 6 g/ml. The mixture is stirred for 5 minutes thoroughly so that a homogenous cement paste is obtained. The past is injected into a cylindrical rubber mould, open at both ends. The mould is then immersed in 40 ml PBS, pH 7.4, at 37° C. and kept in a sealed beaker. After 24 hours, the samples are removed from the mould. For comparison, the described powder composition is mixed directly with water.

CS and ST are measured as described in Example 1.

In Vivo Studies:

A cement with P/L 4.5 with 20% $ZrO_2$ was injected into a drilled defect (~8 mm³) in the vertebra of a rat.

Results:

The amounts of additives, the setting times, and the compressive strengths after 24 hours in PBS at 37° C. are set forth in Table 2:

TABLE 2

| P/L, g/ml | B-TCP/ MCPM, % | $ZrO_2$, % | Cer, % | ST, min | CS, MPa |
|---|---|---|---|---|---|
| 4 | 90 | 10 | — | 30 | 10 |
| 4 | 65 | 15 | 20 | 35 | 7 |
| 4.2 | 75 | 15 | 10 | 28 | 9 |
| 5 | 80 | 20 | — | 18 | 9 |
| 6 | 60 | 40 | — | 20 | 14 |

The results show that an acidic premixed material system with radio-opacity and bioactive fillers with clinically acceptable setting times can be achieved, combined with a strength development. The in vivo studies showed that the cement was resorbed and replaced by bone. The same precursor cement material mixed directly with water had too short of a setting time to mould a sample that could be strength-tested, and no data could thus be obtained.

Example 3

This example demonstrates a hydraulic cement composition according to the invention. Specifically, precursor cement comprising 35 wt % monocalcium phosphate monohydrate ($Ca(H_2PO_4)_2$—$H_2O$, MCPM) (Fluka), 40 wt % β-Tricalcium phosphate ($Ca_3(PO_4)_2$, β-TCP), grain size (d99, volume-weighted) <100 μm, and 25 wt % β-TCP granules (250 μm diameter, 20% porosity) are used. The MCPM and β-TCP powder and granules are first mixed together and then glycerol is added. The P/L ratio is 4. The mixture is stirred thoroughly until a homogenous cement is obtained, which is injected into a rubber mould using a dispensing tip gauge of 1.5 mm. The mould is immersed in 40 ml PBS at 37° C. and kept in a sealed beaker. Filter paper (Whatman 597) is used to cover the bottom of the cylindrical mould to prevent the cement paste from dripping out of the mould while allowing diffusion of water and glycerol. For comparison, the described powder composition was mixed directly with water.

CS and ST are measured as described in Example 1.

Results:

The results show that an acidic premixed material system with clinically acceptable setting time (25 minutes) can be achieved, combined with a strength development (10 MPa). The same precursor cement material mixed directly with water had too short of a setting time to mould a sample that could be strength-tested, and no data could thus be obtained.

Example 4

This example demonstrates an apatitic cement hydraulic cement composition according to the invention. Specifically, a precursor cement comprising 15 wt % monocalcium phosphate monohydrate ($Ca(H_2PO_4)_2$—$H_2O$, MCPM) (Fluka), 50 wt % tetracalcium phosphate ($Ca_4(PO_4)_2O$, TTCP), 15 wt % dicalcium phosphate anhydrous ($CaHPO_4$, DCPA), and 20 wt % β-TCP granules (250 μm diameter, 20% porosity) is used. The TTCP, DCPA, and MCPM powders and the β-TCP granules are first mixed together and then glycerol is added. The P/L is 4. The mixture is stirred thoroughly until a homogenous cement is obtained, which is injected into a rubber mould using a dispensing tip gauge of 1.5 mm. The mould is then immersed in 40 ml PBS at 37° C. and kept in a sealed beaker. Filter paper (Whatman 597) is used to cover the bottom of the cylindrical mould to prevent the cement paste from dripping out of the mould while allowing diffusion of water and glycerol. For comparison, the described powder composition is mixed directly with water.

CS and ST are measured as described in Example 1.
Results:
The results show that an acidic premixed material system with clinically acceptable setting time (9 minutes) can be achieved, combined with a strength development (14 MPa).

Example 5

This example demonstrates a hydraulic cement composition according to the invention. Specifically, a precursor cement comprising $(CaO)_3SiO_2$ and calcium sulfate hemihydrate (alfa phase), both having a grain size below 10 micrometer, is used. The ratio between $(CaO)_3SiO_2$ and calcium sulfate is 3:1, and 1.5 wt % of hydroxypropylmethyl cellulose (HPMC) is added to the powder. $(CaO)_3SiO_2$ and calcium sulfate hemihydrate are first mixed, whereafter the HPMC is added. Finally, glycerol is added. The P/L is 2.5. The mixture is stirred thoroughly until an homogenous cement is obtained, which is then injected into a rubber mould using a dispensing tip gauge of 1.5 mm. The mould is immersed in 40 ml PBS at 37° C. and kept in a sealed beaker. The bottom and the top of the mould are covered with a polycarbonate filter having pore size of 5 μm (Millipore). For comparison, the described powder composition is mixed directly with water using a spatula and a mixing bowl at powder to liquid ratio of 2.5.

CS and ST are measured as described in Example 1. The working time was measured as the possible ejection time through an 11 gauge needle via 5 ml syringe after the mixing operation.
Results:
The results show that a premixed calcium silicate material system with clinically acceptable setting time (25 minutes) can be achieved. For the premixed paste, the working time was indefinite. The strength development (60 MPa) proved a setting and hardening reaction. The material mixed directly with water showed similar reaction rate and compressive strength as the premixed material but had a working time of only 12 minutes. Thus, a clinically acceptable premixed cement can be achieved with a controlled, long working time.

Example 6

This example demonstrates a hydraulic cement composition according to the invention, specifically, a pre-mixed calcium silicate cement with nano-sized grains according to the present invention. A precursor cement comprising ($CaO)_3SiO_2$ having a grain size below 100 nanometers is employed, and 1.5 wt % of HPMC is added to the powder. Glycerol is added, and the P/L is 2. The mixture is stirred thoroughly until a homogenous cement is obtained, which is then injected into a rubber mould using a dispensing tip gauge of 1.5 mm. The mould is immersed in 40 ml PBS at 37° C. and kept in a sealed beaker. The bottom and the top of the mould are covered with a polycarbonate filter having pore size of 5 μm (Millipore). For comparison, the described powder composition is mixed directly with water using a spatula and a mixing bowl at a P/L of 2.

CS and ST are measured as described in Example 1, although the CS is measured after both 1 h and 24 h. The working time was measured as described in Example 5.
Results:
The premixed material shows a compressive strength of 30 MPa and 70 MPa after 1 h and 24 h, respectively. The setting time was below 20 minutes. The material mixed directly with water shows an immediate setting and can not be evaluated. These results demonstrate that a nano-sized calcium silicate-based premixed material system with high strength and clinically acceptable setting time can be achieved.

Example 7

This example demonstrates a hydraulic cement composition according to the invention using a nano-sized premixed acidic cement. Specifically, a cement comprising monocalcium phosphate monohydrate ($Ca_2(H_2PO_4)_2$—$H_2O$, MCPM) as received from the manufacturer, and β-tricalcium phosphate ($Ca_3(PO_4)_2$, β-TCP), grain size <100 nm, in a β-TCP:MCPM molar ratio of 1:1, is used. Two additives, namely 1 vol % polysorbate 20 surfactant and 1.5 wt % HPMC gelling agent, are employed. MCPM and β-TCP are first mixed, whereafter the HPMC is added. The polysorbate is first mixed with glycerol separately and then added to the powder. The P/L is 2.5. The mixture is stirred thoroughly until a homogenous cement is obtained, which is injected into a rubber mould using a dispensing tip gauge of 1.5 mm. The mould is immersed in 40 ml PBS at 37° C. and kept in a sealed beaker. Filter paper (Whatman 597) is used to cover the bottom of the cylindrical mould to prevent the cement paste from running out of the mould while allowing diffusion of water and glycerol. For comparison, the described powder composition was mixed directly with water.

CS and ST are measured as described in Example 1.
Results:
The results show that an acidic premixed material system with clinically acceptable setting time (10 minutes) can be achieved combined with a strength development (17 MPa), proving a setting and hardening reaction. The material mixed directly with water had too short of a setting time to mould a strength sample and no data could be obtained.

Example 8

This example demonstrates a hydraulic cement composition according to the invention. Specifically, a root-canal filling material based on calcium silicate precursor material is formulated, optionally with antibiotics included in the formulation. A precursor cement comprising a mixture of $(CaO)_3SiO_2$ and $(CaO)_2SiO_2$ having a grain size below 20 micrometer is used. Additionally, 20 wt % of $ZrO_2$ with a grain size below 20 micrometer is added to the composition to obtain radio-opacity. In a second experiment, tobramycin (antibiotic) is added to the first formulation (5 wt %) and to a control cement formulation. Glycerol is added to the inventive formulations with a P/L of 2.5. The mixture is stirred thoroughly until a homogenous cement is obtained, which is then injected into a rubber mould using a dispensing tip gauge of 1.5 mm. The mould is immersed in 40 ml PBS at 37° C. and kept in a sealed beaker. The bottom and the top of the mould are covered with a polycarbonate filter having pore size of 5 μm (Millipore). Tests are also performed by injecting the pastes through a 0.5 mm cannula, simulating a root canal filling. For comparison, the described powder composition is mixed directly with water using a spatula and a mixing bowl at powder to liquid ratio of 2.5. Setting time and working time are measured as described in Example 6.

Radio-Opacity:

Radio-opacity is measured on hardened and polished samples (1 mm thick) and compared to Al sheets.

Drug Release:

The drug release from the antibiotics loaded cements is measured as the bacterial growth inhibition zone using the method described by Brohede et al, "Multifunctional implant coatings providing possibilities for fast antibiotics loading with subsequent slow release," *Journal of Materials Science: Materials in Medicine,* 20: 1859-1867 (2009).

Results:

The results show that a premixed calcium silicate material system with clinically acceptable setting time can be achieved. For the premixed paste, the working time is indefinite. The material mixed directly with water shows similar reaction rate and compressive strength as the premixed material but had a working time of 20 minutes, which is low for a clinical application. The radio-opacity was above 2 mm Al (which means that the opacity is higher than for enamel).

The cements also show a prolonged release of antibiotics, generally more than 3 days. This is important in order to have an option for killing remaining bacteria in the root canal.

Example 9

This example demonstrates a hydraulic cement composition according to the invention, specifically, a premixed calcium aluminate cement according to the present invention. A cement comprising $(CaO)Al_2O_3$ and zirconium dioxide in a weight ratio of 3:1 is employed. Both powders have a grain size of below 15 micrometer. Three additives are used, namely 1 wt % polysorbate 20 surfactant, 1.5 wt % HPMC gelling agent, and 0.5 wt % lithium chloride (LiCl). The two powders are first mixed, whereafter the HPMC and LiCl are added. The polysorbate is mixed with glycerol separately before the combined liquid is added to the powder. The P/L is 2.5. The mixture is stirred thoroughly until homogenous cement is obtained, which is injected into a rubber mould using a dispensing tip gauge of 1.5 mm. The mould is immersed in 40 ml PBS at 37° C. and kept in a sealed beaker. The bottom and the top of the mould are covered with a polycarbonate filter having a pore size of 5 μm (Millipore). For comparison, the described powder composition is mixed directly with water to a P/L of 0.4.

CS, ST and working time are measured as described in Example 6.

Results:

The premixed material shows a compression strength of 50 MPa and 70 MPa after 1 h and 24 h, respectively. The setting time is below 25 minutes. The premixed material can be ejected through a 11 G needle for an indefinite time, i.e. it does not set unless brought in contact with water-based liquids. The material mixed with water directly showed a similar strength and setting time but could not be ejected through a 11 G needle 7 minutes after mixing. Thus, when combining a non-aqueous water-miscible liquid and a calcium aluminate cement, a clinically acceptable premixed cement can be achieved with a controlled, long working time.

Example 10

This example demonstrates a hydraulic cement composition according to the invention comprising a premixed calcium aluminate cement with nano-sized grains. The nano-sized materials generally have a more homogenous microstructure, which leads to better mechanical properties. Specifically, a cement comprising $(CaO)Al_2O_3$, $(CaO)_3Al_2O_3$ and microcrystalline silica in a weight ratio of 8:2:1 is used. The powders have a grain size below 0.1 micrometer. Three additives are used, namely, 1 vol % polysorbate 20 surfactant, 1.5 wt % HPMC gelling agent, and LiCl. The two powders are first mixed, whereafter the HPMC and LiCl are added. The polysorbate is mixed with glycerol separately before the combined liquid is added to the powder. The P/L is 2, and the mixture is stirred thoroughly until a homogenous cement is obtained, which is injected into a rubber mould using a dispensing tip gauge of 1.5 mm. The mould is immersed in 40 ml PBS at 37° C. and kept in a sealed beaker. The bottom and the top of the mould are covered with a polycarbonate filter pore size of 5 μm (Millipore). For comparison, the described powder composition is mixed directly with water with a P/L of 2.

CS, ST and working time are measured as described in Example 6.

Results:

The premixed material shows a compressive strength of 70 MPa and 90 MPa after 1 h and 24 h, respectively. The setting time is below 20 minutes. The water-mixed material showed an immediate setting and could not be evaluated. These results show that a nano-sized calcium aluminate-based premixed material system with high strength and clinically acceptable setting time can be achieved.

The specific embodiments and examples described herein are exemplary only in nature and are not intended to be limiting of the invention defined by the claims. Further embodiments and examples, and advantages thereof, will be apparent to one of ordinary skill in the art in view of this specification and are within the scope of the claimed invention.

What is claimed is:

1. A non-aqueous, hydraulic cement-forming composition, comprising a non-aqueous mixture of (a) a non-hydrated powder composition comprising at least 50 weight % calcium silicate powder, and one or more components selected from the group consisting of (i) β-tricalcium phosphate (β-TCP), and (ii) calcium sulfate, (b) non-aqueous water-miscible liquid, wherein the weight to volume (g/ml) ratio of the powder composition to the non-aqueous water-miscible liquid is in a range of about 1:1 to about 5:1, and (c) at least one agent effective to increase the radio-opacity of a cement formed from the composition.

2. The hydraulic cement-forming composition of claim 1, wherein the powder composition comprises from about 5 to about 30 weight % of a mixture of (i) β-tricalcium phosphate (β-TCP), and (ii) monocalcium phosphate monohydrate and/or anhydrous monocalcium phosphate.

3. The hydraulic cement-forming composition of claim 1, wherein the powder composition comprises from about 5 to about 30 weight % of calcium sulfate powder.

4. The hydraulic cement-forming composition of claim 1, wherein the powder composition further comprises from about 0.1 to about 15 weight % of a magnesium-containing powder.

5. The hydraulic cement-forming composition of claim 1, comprising a pH regulating agent and/or a hardening accelerator.

6. The hydraulic cement-forming composition of claim 1, wherein the non-aqueous water-miscible liquid comprises glycerol.

7. The hydraulic cement-forming composition of claim 1, wherein the powder composition comprises nanopowders having a grain size of less than 1 micron.

8. The hydraulic cement-forming composition of claim 1, further comprising one or more components selected from the group consisting of a surfactant operable to facilitate diffusion of water into the composition, a porogen operable to provide a macroporous structure upon hydration, a gelling agent operable to enhance cohesiveness of the composition, and reinforcing fiber.

9. The hydraulic cement-forming composition of claim 1, further comprising an active pharmaceutical ingredient.

10. The hydraulic cement-forming composition of claim 1, wherein the powder composition comprises nanopowders having a grain size of less than 500 nm.

11. The hydraulic cement-forming composition of claim 1, wherein the powder composition comprises nanopowders having a grain size of less than 300 nm.

12. The hydraulic cement-forming composition of claim 1, further comprising one or more agents selected from the group consisting of an anti-cancer agent, an antibacterial agent, an analgesic agent, a bisphosphonate, a bone growth promoter, and an anti-inflammatory agent.

13. The hydraulic cement-forming composition of claim 1, wherein the at least one agent effective to increase the radio-opacity of a cement formed from the composition comprises iodine, a strontium compound, a barium compound, a bismuth compound, zirconium dioxide, or a combination thereof.

14. The hydraulic cement-forming composition of claim 1, comprising from about 5 to about 40 weight % of the at least one agent effective to increase the radio-opacity of a cement formed from the composition.

15. A method of producing a hardened cement, comprising contacting the hydraulic cement-forming composition of claim 1 with a hydration liquid or vapor.

16. A hardened cement comprising a product formed by contacting the hydraulic cement-forming composition of claim 1 with a hydration liquid or vapor, the hardened cement comprising calcium silicate hydrate.

17. An article of manufacture comprising the hydraulic cement-forming composition of claim 1 in a dispensing container.

18. An article of manufacture comprising the hydraulic cement-forming composition of claim 1 in a dispensing syringe.

19. A non-aqueous, hydraulic cement-forming composition, comprising a non-aqueous mixture of (a) a non-hydrated powder composition comprising at least 50 weight % calcium silicate powder, and one or more components selected from the group consisting of (i) β-tricalcium phosphate (β-TCP), and (ii) calcium sulfate, (b) non-aqueous water-miscible liquid, wherein the weight to volume (g/ml) ratio of the powder composition to the non-aqueous water-miscible liquid is in a range of about 1:1 to about 4:1, and (c) from about 5 to about 40 weight % of at least one agent effective to increase the radio-opacity of a cement formed from the composition.

20. The hydraulic cement-forming composition of claim 19, wherein the at least one agent effective to increase the radio-opacity of a cement formed from the composition comprises iodine, a strontium compound, a barium compound, a bismuth compound, zirconium dioxide, or a combination thereof.

21. The hydraulic cement-forming composition of claim 19, further comprising at least one active pharmaceutical ingredient selected from the group consisting of an anti-cancer agent, an antibacterial agent, an analgesic agent, a bisphosphonate, a bone growth promoter, and an anti-inflammatory agent.

22. A method of producing a hardened cement, comprising contacting the hydraulic cement-forming composition of claim 19 with a hydration liquid or vapor.

23. A hardened cement comprising a product formed by contacting the hydraulic cement-forming composition of claim 19 with a hydration liquid or vapor, the hardened cement comprising calcium silicate hydrate.

* * * * *